«12» United States Patent
Kahol et al.

(10) Patent No.: US 6,833,143 B1
(45) Date of Patent: Dec. 21, 2004

(54) PROCESS FOR THE PREPARATION OF A EXTRACT RICH IN BACOSIDES FROM THE HERB *BACOPA MONNIERA*

(75) Inventors: Atul Prakash Kahol, Lucknow (IN); Tarun Singh, Lucknow (IN); Sudeep Tandon, Lucknow (IN); Madan Mohan Gupta, Lucknow (IN); Suman Preet Singh Khanuja, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/400,192

(22) Filed: Mar. 26, 2003

(51) Int. Cl.$^7$ .............................................. A61K 35/78
(52) U.S. Cl. ....................................................... 424/725
(58) Field of Search ........................................... 424/725

(56) References Cited

U.S. PATENT DOCUMENTS 6,261,605 B1 * 7/2001 Singh-Verma .............. 424/725
2003/0157201 A1 * 8/2003 Pandita et al. .............. 424/725

OTHER PUBLICATIONS

Parrotta, John. Healing Plants of Peninsular India. 1991. CABI Publishing, New York, NY, p. 660.*
Singh et al. Indian J. Pharmacol. 1997. vol. 29, No. 5, pp. S359–S365, BIOSIS Abstract enclosed.*
Sairam et al. Phytomedicine. 2002. vol. 9, No. 3, pp. 207–211, CAPLUS Abstract enclosed.*
Chatterjea et al. Indian J. Chem. 1963. vol. 1, pp. 212–215. CAPLUS Abstract enclosed.*

* cited by examiner

*Primary Examiner*—Christopher R. Tate
(74) *Attorney, Agent, or Firm*—Perkins Coie LLP

(57) ABSTRACT

The present invention provides a novel process for the preparation of bacosides enriched fraction in a non-hygroscopic form the extract of *Bacopa monniera*, the said process comprising the steps of drying freshly harvested herb in a hot air oven at 37–42° C., powdering and sieving the dried herb to obtain powder of 30–40 mesh size, defatting the powdered herb with hexane in a modified soxhlet extractor, extracting the defatted powdered herb with acetone, again extracting the same herb with methanol to obtain an extract containing bacosides, concentrating the extract to one twentieth of its original volume under reduced pressure, gradually adding the concentrated extract to acetone for precipitating the bacosides, filtering the bacosides in a Nutsche type vacuum filter, dissolving the crude bacoside mass into 2–10 parts water, extracting the bacoside solution with n-butanol to selectively transfer the bacosides to the solvent phase, separating and concentrating the solvent phase under vacuum to obtain semi-dry mass, dissolving the semi dried mass into 2–10 parts water, adding and stirring 1–5% of β-cyclodextrin to stabilize the bacosides, spray drying the stabilized bacoside solution by maintaining hot air temperature at 90–110° C., to obtain a stable free flowing fraction of *Bacopa monniera* rich in bacosides.

14 Claims, No Drawings

PROCESS FOR THE PREPARATION OF A EXTRACT RICH IN BACOSIDES FROM THE HERB BACOPA MONNIERA

FIELD OF THE INVENTION

The present invention relates to an improved process for the preparation of stable bacosites enriched fraction in non-hygroscopic form from the herb *Bacopa monniera*.

BACKGROUND AND PRIOR ART

Plant based drugs and formulations are showing a rising trend globally for the health care due to the biosafe attributes they possess over modern synthetic medicines. Amongst the numerous traditional Indian medicinal herbs, standardized extract of *Bacopa monniera* known as 'Brahmi' in Hindi is finding increasing use as a constituent of modern herbal nutraceuticals aimed at supporting brain and nerve function and enhancing memory, alertness & mental concentration (Ray Sahelian, M.D. "Mind Boosters", 1999, Amazon Publishing House, USA).

*Bacopa monniera* has been used in India since ancient times in Ayurvedic preparations as a brain and a nerve tonic (Chunekar K C, "Bhav Prakasha Nighantu", Hindi translation, Varanasi, 1960: 372). In a clinical trial carried out at the Banaras Hindu University. (Singh R H and Singh Lallan, "Studies on the Anti-anxiety effect of the Medhya Rasayana Drug, Brahmi *Bacopa monniera* Wettst. Part 1, *Journal of Res. Ayurveda & Sidha* Vol 1: 133–148, 1980). *Bacopa monniera* in the form of brahmi syrup when administered to 35 patients suffering from anxiety neurosis, it was concluded that 4 weeks of treatment with brahmi significantly reduced the level of anxiety amongst the patients with improvement in the mental performance and memory of the treated patients. The beneficial effects of *Bacopa monniera* on the intelligence and mental performance were further investigated at Banaras Hindu University in a trial carried out on 20 school children over a period of three months. (Sharma R, Chaturvedi C, Tewari P V, "Efficacy of *Bacopa monniera* in revitalizing intellectual functions in Children" *Journal Res. Edu, Ind Med*, Jan–Jun.: 1–12, 1987).

Systematic Chemical Examination of *Bacopa monniera* was first reported by N Chatterjee, R P Rastogi & M L Dhar, (*Indian Journal of Chemistry*, Vol 1, May 1963). They reported the occurrence of two saponins designated as Bacoside A & B which are present in a concentration of over 2% in the dry plant. The molecular structure of the bacosides A & B was subsequently elucidated. (Chatterjee N, Rastogi R P and Dhar M L, *Indian J Chem*, Vol 3: 24, 1965 and Basu N, Rastogi P and Dhar M L, *Indian J Chem* Vol 5: 84, 1967). These studies also reported the physical properties of the bacosides A&B:

| | |
|---|---|
| Bacoside A, | Melting Point = 250.6° C. (decomposition), Optical Rotation $\alpha_D$ = (−) 42° in Ethanol |
| Bacoside B, | Melting Point = 203° C. (decomposition), Optical Rotation $\alpha_D$ = (+) 8° in Ethanol |

An analytical method based on high performance thin layer chromatography (HPTLC), for the determination of bacoside-A content in *Bacopa monniera* has been reported by Gupta et al (A P Gupta, S Mathur, M M Gupta & Sushil Kumar, "Effect of the method of drying on the bacoside-A content of the harvested *Bacopa monniera* shoots revealed using a high performance thin layer chromatography method", *Journal of Medicinal and Aromatic Plants* Vol, 20: 1052–1055, 1998). The bioactivity of *Bacopa monniera* extract has been studied by evaluating the avoidance responses in Rats in an extensive trial carried out at the Central Drug Research Institute, Lucknow, India (H K Singh, R P Rastogi, R C Srimal and B N Dhawan, *Phytotherapy Research*, Vol 2 (2): 70–75, 1988). It has been concluded in this study that Bacosides A & B are the active constituents of *Bacopa monniera* which are responsible for the enhanced mental performance and retention capacity.

The authentication of the traditional claims of brahmi was investigated at the Central Drug Research Institute by studying the effect of alcoholic extract of this plant on acquisition, consolidation and retention of the three memory related behavioral responses in albino rats. (Singh H K and Dhawan B N, "Neuropsychopharmacological effects of the Ayurvedic nootropic *Bacopa monniera* Linn (Brahmi)", *Indian Journal of Pharmacology*, Vol 29 (5): S359–S365, 1997). In this study, bacosides were also found to be safe in regulatory, pharmacological and toxicological studies carried out on normal healthy male volunteers. This study was designated as Phase-I clinical trial. *Bacopa* extract was administered to human volunteers for 4 weeks in single and multiple doses in double blind placebo controlled and non-crossover regulatory clinical trial. The mechanism of action of the facilitatory effect of bacosides was attributed to their enhanced protein kinase activity and production of an increased level of protein in hippocampus. Another conclusion of this study was that the bacosides attenuated the retrograde amnesia produced by immobilization induced stress and scopolamine. P A Thakurdesai, P L Kole and A. N Nagappa (www.Pharmabiz.com/newsfeat/feat/112.com) have stressed the necessity of using standardized extracts for achieving desired efficacy.

Considering the great importance and potential of bacosides, derived from *Bacopa monniera*, in human health, the information about an efficient process suitable for industrial production is not available in the literature. Patent literature also does not disclose any information on the subject of efficient production technology of bacosides. The literature contains a few lab scale methods for the preparation of an extract of *Bacopa monniera* containing bacosides. The method of isolation adopted by Chatterjee et al (N Chatterjee, R. P. Rastogi & M. L. Dhar, *Indian Journal of Chemistry*, Vol 1, May 1963; Chatterjee N, Rastogi R P and Dhar M L, *Indian J Chem*, Vol 3: 24, 1965) and further modified by Singh et al (H K Singh, R P Rastogi, R C Srimal and B N Dhawan, *Phytotherapy Research*, Vol 2 (2): 70–75, 1988), describes the extraction of the *Bacopa monniera* dried herb with alcohol, wherein the dried herb material is first moistened with water and then extracted with alcohol, which is concentrated under reduced pressure and repeatedly macerated with benzene for defatting. The filtrate is diluted to 60% concentration of alcohol and is treated with an excess of lead acetate. The lead salts are filtered and the residual lead was removed from the filtrate with hydrogen sulphide. The pH of the filtrate is adjusted to 6.4 with sodium carbonate and concentrated at 50° C. under vacuum to one third of its volume and partitioned repeatedly with butanol & water. The butanol fraction on concentration under vacuum deposits a powder containing bacosides A&B. The powder is then crystallized from alcohol as colourless needles. An additional amount of bacosides is obtained from the filtrate by freeing it from solvent and macerating the residue with acetone. This method apart from being very tedious and time consuming involves the use of benzene (potentially carcinogenic) and lead salt (highly poisonous). Although the process attempts to remove the residual lead with hydrogen sulphide gas, the complete removal is doubtful in view of involvement of gas-liquid mass transfer where high efficiencies are difficult to achieve. The presence of these toxic chemicals even in traces will make the quality of the final product questionable. This method is not suited for scaling up to industrial production due to being tedious and health hazardous. In the method adopted for the study carried out by H K Singh and B N Dhawan (Journal of Ethanopharmacology, Vol 5: 205–214, 1982), to evaluate the effect of brahmi extract on avoidance responses in rats, the air dried plant material is extracted with 90% ethanol by soxhlet extraction apparatus and the extract obtained is mixed with 10% gum acacia for feeding the rats. In this study no attempt was made to monitor the bacosides contents of the extracts. In an another study carried out at the University of Madras on the anti cancer activity of *Bacopa monniera* (V. Elangovan, S Govindasamy, N Ramamoorthy and K. Balasubramanian, "In vitro studies on the anticancer activity of *Bacopa monniera, Fitoterapia*, Vol LXVI (3): 211–215, 1995), the procedure for the extraction of bacosides consists of soaking the powdered plant material in 95% ethanol for 48 hr, concentrating the extract under vacuum and drying it by lypholisation. No attempt was made to measure the bacoside concentration of the extract. Standardised extract of *Bacopa monniera* containing 20–30% bacosides A&B is being manufactured and marketed by a few commercial firms, but the process of production is not disclosed. (Product Information Brochure of M/s Sabinsa Corporation, 121, Ethel Road West, Piscataway, N.J. 08854, USA and M/s Himalaya USA, M/s Velvette International, Chennai, India, M/s Dalmia Industries Ltd, India).

A major problem encountered during the process was the difficulty of obtaining the stable final product in the form of a dry free flowing powder as the active constituents (bacosides) are highly hygroscopic.

OBJECTS OF THE INVENTION

The main object of the present invention is to provide an improved process for the preparation of bacosites enriched fraction in non-hygroscopic form from the herb *Bacopa monniera* overcoming the disadvantages of the hitherto known processes.

Another object of the present invention is to provide an improved process for preparation of bacosites enriched fraction from *Bacopa monniera* using relatively non toxic solvents like hexane, acetone and methanol.

Yet another object of the present invention is to provide an improved process for removing unwanted constituents of *Bacopa monniera* herb by extracting the defatted herb with acetone.

Still another object of the present invention is to provide an improved process for stabilization of bacoside containing extract by addition of non-toxic stabilizing agents such as mannitol, maltodextrin, β-cyclodextrin or polyvinyl alcohol.

One more object of the present invention is to provide an improved process for purifying the *Bacopa monniera* extract using a countercurrent 'KARR' liquid—liquid extraction column fitted with a reciprocating agitator.

SUMMARY OF THE INVENTION

Accordingly, the present invention provides an efficient process for the preparation of stable bacosites enriched fraction in non-hygroscopic form from the herb *Bacopa monniera*.

DETAILED DESCRIPTION OF THE INVENTION

The present invention provides an improved process for preparing stable bacosides enriched fraction in a non-hygroscopic form the extract of herb *Bacopa monniera*, the said process comprising the steps of:

(i) drying freshly harvested *Bacopa monniera* herb in an oven at a temperature range of 37–42° C. for a time period of 4–6 hrs;

(ii) grinding and sieving the dried herb of step (i) in a disintegrator to obtain ground herb;

(iii) extracting the ground herb of step (ii) with hexane in a modified soxhlet apparatus to obtain a hexane extract;

(iv) removing the hexane extract formed in step (iii) from the soxhelt and drying the herb by circulating hot water;

(v) extracting the dried herb of step (iv) with acetone for a time period of 4 to 8 hours to obtain an acetone extract containing unwanted color and non-bacoside constituents;

(vi) extracting the acetone extracted herb of step (v) with methanol to obtain a methanol extract containing bacosides;

(vii) concentrating the methanol extract of step (vi) under reduced pressure;

(viii) adding the concentrated methanol extract of step (vii) gradually to acetone with stirring to effect preferential precipitation of crude bacosides;

(ix) filtering the crude bacosides of step (viii) in a Nutsche type vacuum filter to obtain a crude bacoside residue;

(x) dissolving the crude bacoside residue of step (ix) with water to obtain an aqueous solution;

(xi) extracting the aqueous solution of step (x) with n-butanol to obtain a n-butanol extract;

(xii) concentrating the n-butanol extract of step (xi) in a rotary vacuum evaporator under high vacuum to obtain a dry residue rich in bacosides;

(xiii) dissolving the dry residue of step (xii) in 2 to 10 parts of water, adding 1 to 5 wt. % of a non-toxic stabilizer under constant stirring to obtain a stable bacoside solution, and (xiv) spray drying of the stable bacoside solution of step (xiii) at a temperature ranging between 90–110° C. to obtain bacosides in the form of a free flowing, stable and non-hygroscopic powder.

In an embodiment of the present invention wherein in step (ii), the particle size of the ground herb is in the range of 30–40 mesh.

In another embodiment of the present invention wherein in step (iii), the dried *Bacopa monniera* herb is extracted in a modified soxhlet extractor wherein the drug holder is provided with a hot water jacket.

In yet another embodiment of the present invention wherein in step (iii), the ground herb is extracted with hexane to effect defatting of the herb.

In still another embodiment of the present invention wherein in step (iv), the herb is dried by circulating hot water in the temperature range of 70–75° C. through the jacket.

In one more embodiment of the present invention wherein in step (vii), the extract containing bacosides is concentrated to one twentieth of its original volume.

In one another embodiment of the present invention, the extract is concentrated using an agitated wiped film evaporator under high vacuum at a temperature range of 45 to 55° C.

In a further embodiment of the present invention wherein in step (viii), crude bacosides are precipitated from the concentrated methanol extract by stirring with excess quantity of acetone.

In an embodiment of the present invention, the w/w ratio of the methanol extract and acetone is in the range of 1:4 to 1:10.

In another embodiment of the present invention wherein in step (xi), n-butanol is used as a selective solvent to enrich the concentration of bacosides thereby resulting in greater product purity.

In yet another embodiment of the present invention wherein in step (xi), the *Bacopa monniera* extract may be purified efficiently using countercurrent 'KARR' liquid—liquid extraction column fitted with a reciprocating agitator.

In still another embodiment of the present invention wherein in step (xiii), the non-toxic stabilizing agent used is selected from the group consisting of mannitol, maltodextrin, β-cyclodextrin or polyvinyl alcohol.

In one more embodiment of the present invention, the yield of bacosides with respect to dry weight of *Bacopa monniera* ranges between 1.5 to 2.5%.

In one another embodiment of the present invention, the powder obtained contains 2030% bacosides A and B.

In a further embodiment of the present invention, the percentage of bacosides in the powder is estimated by HPTLC analysis.

In accordance with the method of invention, the initial process step consists of drying the freshly harvested herb in a tray type hot air oven at 37–42° C. for 4–8 hours. Care is taken to spread the herb in a thin layer 2–3 inch thick uniformly over the perforated drying tray for even drying. A sample of the herb is tested for moisture content which should preferably be between 3.5 to 5.5%. The dried herb is then powdered in a disintegrator. The resulting course powder is sieved in a 30 mesh sieve and oversized material is recycled back to the disintegrator. The powdered dried herb is charged to the drug holder of the modified soxhlet apparatus along with the hydrocarbon solvent 'hexane'. This solvent has been chosen for its ability to remove the unwanted lipids, plant waxes and part of the colouring matter. Also, bacosides are totally insoluble in hexane and are left intact in the plant material. Several percolations are carried out to achieve complete defatting of *Bacopa monniera* herb over a period of 4–8 hours. After the completion of the extraction the hexane extract is removed for recovery of solvent and the bed of *Bacopa monniera* is dried by passing hot water at 70–75° C. in the drug holder jacket. The same bed of herb is then extracted with a moderately polar solvent 'Acetone' over a period of 4–8 hours. The second extraction of the herb with acetone in which the bacosides are insoluble, is carried out to remove the maximum remaining unwanted constituents and colouring matter from the herb. After the extraction the acetone extract is removed for recovery of solvent and the bed is dried following the previous procedure. The bed is next extracted for a further period of 4–8 hours using a high polarity solvent 'Methanol' which dissolves the bacosides and also other minor constituents. The methanolic extract is then removed from the soxhlet apparatus and concentrated to one twentieth of its original volume under vacuum in a rotary vacuum evaporator at a temperature 45–55° C. The concentrated extract containing bacosides is slowly added to a stirred vessel containing 1–4 parts acetone to precipitate bacosides A&B along with some other acetone insoluble material. The slurry is filtered in a Nutsche type vacuum filter to remove the solvent. The precipitate is next dissolved in 2–10 parts of water. This solution is extracted with a solvent of high polarity immiscible with water to transfer the bacosides to the solvent phase. We have selected n-butanol as the solvent for this step as it meets the requirements of high selectivity for bacosides and it is also immiscible with water. The butanol extract is concentrated under high vacuum at a temperature of 50–55° C. in a rotary vacuum evaporator. The effectively dried mass is dissolved in 2–10 parts water in a stirred vessel and β-cyclodextrin (1–5%) is added as stabilizer. Other stabilizing agents such as mannitol, maltodextrin, polyvinyl alcohol are also suitable for this purpose. Stirring is continued for 1–2 hours. Solution is next fed to a hot air spray drier fitted with a spray nozzle and a cyclone device for collecting the product. The flow rates of the air and solution and hot air temperature are carefully controlled to obtain the bacosides mixture as a buff coloured, free flowing and non-hygroscopic powder. The percentage of the bacosides in the final product is estimated by HPTLC procedure as reported by Gupta et al. (A P Gupta, S Mathur, M M Gupta & Sushil Kumar, *Journal of Medicinal and Aromatic Plants*, 20: 1052–1055, 1998). By following the process of this invention a product containing 20–30% bacosides A&B is obtained. The yield of the product based on the dry weight of *Bacopa monniera* ranges between 1.5–2.5%. This standardized extract of *Bacopa monniera* is quite stable and suitable for formulating into nutraceuticals.

The process of the present invention is illustrated by following examples which should not be construed to limit the scope of the present invention. The following examples also illustrate the specific embodiments of the method of invention.

EXAMPLE 1

1.0 Kg of *Bacopa monniera* herb cultivated at CIMAP farm was shade dried at 30° C. for 24 hours and then in a tray type hot air oven at 42° C. for a period of 8 hours. The herb was evenly spread in 3" layers on the perforated trays of the oven. After drying the moisture content of a sample of the herb was checked and evaluated to be 4.5%. The dried herb was then powdered in a disintegrator and the course powder was passed through a 30 mesh size screen. The oversized material was recycled back to the disintegrator. 400 gms of the powdered dried herb was charged to the drug holder of the modified glass soxhlet apparatus. 2.5 liters of hexane was taken in the reboiler flask and heated over water bath to boil the solvent and start the circulation of the solvent through the herb bed. The soxhlet was operated in this manner continuously for a period of 5 hours to defatt the herb material. The hexane extract was removed for recovery of the solvent. Hot water at 70–75° C. was then passed through the jacket of the modified drug holder of the soxhlet apparatus to dry the herb bed by evaporating the residual solvent. 2.5 liter of the solvent acetone is next taken in the reboiler flask and heated over the water bath to start the circulation of the solvent through the herb bed. The soxhlet was operated for a period of 5 hours to remove the unwanted constituents and colouring matter from the herb. The acetone extract was then removed from the reboiler flask for recovery of the solvent and the herb bed was dried in the same manner as above. After drying, the herb bed was then given a third extraction with 2.5 liter methanol solvent. The soxhlet was operated for a period of 6 hours to completely dissolve the bacosides. The methanolic extract was then removed from the soxhlet apparatus and transferred to a rotary vacuum evaporator to recover the solvent. The extract was concentrated to a final volume of about 100 ml. The concentrated extract containing bacosides was slowly added to a stirred vessel containing 400 ml acetone to precipitate bacosides along with some other acetone insoluble material. The slurry was filtered in a Nutsche type vacuum filter to remove the solvent. The precipitate was next dissolved in 50 ml of water. This solution was then extracted 5×15 ml n-butanol to transfer the bacosides to the solvent phase. The two phases were separated and the butanol extract was transferred to a rotary vacuum evaporator and concentrated under high vacuum at a temperature of 50–55° C. The effectively dried mass (9.80 gm) containing bacosides was dissolved in 100 ml water in a stirred vessel and 0.2 gm β-cyclo dextrin was added to the solution as stabilizer. Stirring was continued for a further period of 1.5 hours. The solution was next fed to a hot air spray drier fitted with a spray nozzle and a cyclone device for collecting the product. The hot air temperature at the cyclone was maintained at 100–110° C. The final product (7.80 gms) was recovered as a buff coloured, free flowing and non-hygroscopic powder. The percentage of the bacoside A in the product was estimated by HPTLC procedure. 5.0 mg of the sample was dissolved in 2 ml methanol. The sample along with standard bacoside A were applied on TLC plates (60$F_{254}$, silica gel, Merck) and run in ethyl acetate:methanol:distilled water (60:14:10). The plates were developed to a height of 8 cm and spots were visualized by immersing the plate in vanillin-sulphuric acid reagent (vanillin: sulphuric acid: ethyl acetate –1 g: 5 ml: 5 ml) followed by heating of the plates at 110° C. for 15 min. The blue coloured bacoside-A spot was scanned at 620 nm and 430 nm using dual wavelength adsorption-reflection mode with background subtraction and using a light slit 1×2 (0.4 mm height×1.2 mm width: using Shimadzu CS930 densitometer). A calibration curve, plotted using varying amounts of bacoside-A, was used for estimating % bacoside-A content in the sample. By following this process of this invention a product containing 28% bacoside A was obtained. The yield of the product based on the dry weight of *Bacopa monniera* was 1.95%.

EXAMPLE 2

The same process was carried out on pilot plant scale using 35 Kg dried *Bacopa monniera* herb, but using stainless steel pilot plant equipment. 150 Kg *Bacopa monniera* herb cultivated at CIMAP farm was shade dried at 32° C. for 24 hours and further dried in a hot air tray type oven at 40–42° C. for 8 hours to final moisture content of 4%. The dried herb material was grinded in the disintegrator to about 30-mesh size. 35 Kg of the dried herb material was loaded to the drug holder of the stainless steel soxhlet plant. 200 liters of hexane solvent was pumped into the drug holder to completely immerse the herb material. After a contact time of 2.0 hours the extract was drained into the reboiler kettle (Vol of extract: 165 It). Steam at 10 psig line pressure was admitted into the jacket of the reboiler kettle to distill the hexane which was sprayed back onto the drug holder to a level of 2" above the herb bed level. A contact time of 2.0 hours was allowed for the second wash. The third and fourth wash was given following the same procedure as above. Hexane was recovered from the extract by distillation and dark coloured residue rejected. The residual solvent adhering to the herb was recovered by circulating hot water at 75° C. in the jacket of the drug holder. After drying of the herb bed, 200 It acetone at 27° C. was next pumped to the drug holder to completely immerse the dry defatted herb. Four washes with a contact time of 2.0 hours each were given to the herb for the removal of the unwanted constituents & colouring matter. The acetone extract was distilled for recovery of solvent. The herb bed was dried following the same procedure as above. After drying, 200 liter of methanol was pumped into the drug holder. Four washes of 2.0 hours each was given to the herb for dissolving the bacosides. The methanol extract was concentrated to one half its volume in the reboiler kettle of the Soxhlet. Concentrate was transferred to a stainless steel agitated wiped thin film evaporator (WFE) for further processing. System was maintained under vacuum of 275 mbar. The rpm of teflon wiper was set at 290 rpm and hot water at 60° C. was circulated in the evaporator jacket. From the WFE processing, 10.5 liter of concentrated extract was obtained. The extract was then slowly transferred to a stainless steel vessel fitted with a mechanical agitator containing 45 liter acetone. The stirring of the solution was continued for 1 hour. The contents were then transferred to a closed stainless steel vacuum filter to remove the solvent acetone. The filter cake was removed and dissolved in 8 liter water. The solution was then transferred to a "KARR" liquid—liquid extraction column fitted with a reciprocating agitator. The aqueous solution was contacted with 10 liter n-butanol in the liquid—liquid extraction column in the counter current mode, to transfer the bacosides into the butanol phase. The butanol phase was then pumped into the stainless steel agitated wiped thin film evaporator for concentrating the extract under high vacuum of 5–10 torr at a temperature of 45–50° C. The concentrated mass containing the bacosides (1.00 kg) was dissolved in 4.0 liter water in a stainless steel stirred vessel and 18 gm of β-cyclodextrin was added to the solution as stabilizer and stirred for a period of 1.5 hours. The solution was next fed to the hot air spray drier fitted with a spray nozzle and a cyclone device for collecting the product. The hot air temperature at the cyclone was maintained at 100–110° C. The product (710 gms) containing bacosides was obtained as a buff coloured, free flowing and non-hygroscopic powder. Yield based on dry herb basis: 2.02%. The content of the bacosides in the product was estimated by the HPTLC method, following the analytical procedure as illustrated in Example 1, percentage bacoside A in the product is 26%.

NOVELTY OF THE INVENTION

1. The improved process achieves the production of bacoside rich extract from *Bacopa monniera* by using relatively non toxic solvents like hexane, acetone and methanol, unlike the prior art process which requires the use of toxic and potentially carcinogenic chemicals like benzene and lead salts.

2. In the improved process the defatting of the herb is carried out using hexane in stead of benzene. Hexane has the advantage of having lower boiling point and 18% lower latent heat of vaporization which results in lesser process heat cost and more significantly, lower level of residual solvent in case of hexane.

3. The improved process employs a modified soxhlet extractor wherein the drug holder is provided with a hot water jacket. This arrangement is useful to remove by evaporating the residual first solvent from the herb bed before starting extraction with the second solvent, thus enabling extraction with multiple solvents in the same extraction system. None of the prior art processes provide any information about the extraction device and techniques used by them.

4. It has been observed that the bacosides containing extract obtained from *Bacopa monniera* has a highly hygroscopic nature which is very difficult to dry and renders its further formulation extremely difficult and inaccurate. The prior art process reported by V Elangovan et al have utilized lypholisation for drying the *Bacopa monniera* extract for using in their experimental studies. Lypholisation as a drying technique is time consuming and requires generation of very low temperature and high vacuum of the order of $10^{-3}$–$10^{-4}$ mbar which has to be achieved with capital intensive equipment and energy intensive operation. The improved process of this invention makes use of spray drying of stabilized extract, as a speedier low cost alternative to obtain the final product as a non-hygroscopic and free flowing powder with uniform particle size.

5. The stabilization of the bacoside containing extract is achieved in the improved process by the judicious use (at 1–5% level) of non-toxic stabilizing agents such as mannitol, maltodextrin, β-cyclodextrin, Polyvinyl alcohol which are well accepted as expients in the pharmaceutical formulations. The stabilization of the bacoside containing extract of *Bacopa monniera* has not been reported so far.

6. The prior art process results in an extract which has an unpleasant bitter taste. It also has a dark green colour. Since the *Bacopa monniera* extract is to be used for formulating nutraceuticals & health foods, a palatable taste and lighter shade of the extract is of paramount importance for achieving a final formulation having a pleasant taste and aesthetic appearance. The process of this invention is able to remove the bitter taste components by the use of selective solvents.

What is claimed is:

1. An improved process for preparing a bacosides-enriched fraction in a non-hygroscopic form from an extract of the herb *Bacopa monniera*, the said process comprising the steps of:

(i) drying freshly harvested *Bacopa monniera* herb in an oven at a temperature range of 37–42° C. for a time period of 4–6 hrs;

(ii) grinding and sieving the dried herb of step (i) in a disintegrator to obtain ground herb;

(iii) extracting the ground herb of step (ii) with hexane in a modified soxhlet apparatus to obtain a hexane extract;

(iv) removing the hexane extract formed in step (iii) from the soxhelt and drying the herb by circulating hot water;

(v) extracting the dried herb of step (iv) with acetone for a time period of 4 to 8 hours to obtain an acetone extract containing unwanted color and non-bacoside constituents;

(vi) extracting the acetone extracted herb of step (v) with methanol to obtain a methanol extract containing bacosides;

(vii) concentrating the methanol extract of step (vi) under reduced pressure;

(viii) adding the concentrated methanol extract of step (vii) gradually to acetone with stirring to effect preferential precipitation of a crude bacosides preparation;

(ix) filtering the crude bacosides of step (viii) in a Nutsche type vacuum filter to obtain a crude bacoside residue;

(x) dissolving the crude bacoside residue of step (ix) with water to obtain an aqueous solution;

(xi) extracting the aqueous solution of step (x) with n-butanol to obtain a n-butanol extract;

(xii) concentrating the n-butanol extract of step (xi) in a rotary vacuum evaporator under high vacuum to obtain a dry residue rich in bacosides;

(xiii) dissolving the dry residue of step (xii) in 2 to 10 parts of water, adding 1 to wt. % of a non-toxic stabilizer under constant stirring to obtain a stable bacoside solution, and (xiv) spray drying the stable bacoside solution of step (xiii) at a temperature ranging between 90–110° C. to obtain a bacosides-enriched fraction in the form of a free flowing, stable and non-hygroscopic powder.

2. A process as claimed in claim 1 wherein in step (ii), the particle size of the ground herb is in the range of 30–40 mesh.

3. A process as claimed in claim 1 wherein in step (iii), the dried *Bacopa monniera* herb is extracted in a modified soxhlet extractor wherein the drug holder is provided with a hot water jacket.

4. A process as claimed in claim 1 wherein in step (iii), the ground herb is extracted with hexane to effect defatting of the herb.

5. A process as claimed in claim 1 wherein in step (iv), the herb is dried by circulating hot water in the temperature range of 70–75° C. through the jacket.

6. A process as claimed in claim 1 wherein in step (vii), the extract containing bacosides is concentrated to one twentieth of its original volume.

7. A process as claimed in claim 6, wherein the extract is concentrated using an agitated wiped film evaporator under high vacuum at a temperature range of 45 to 55° C.

8. A process as claimed in claim 1 wherein in step (viii), the crude backsides preparation is precipitated from the concentrated methanol extract by stirring with excess quantity of acetone.

9. A process as claimed in claim 8, wherein the w/w ratio of the methanol extract and acetone is in the range of 1:4 to 1:10.

10. A process as claimed in claim 1 wherein in step (xi), the *Bacopa monniera* extract is purified efficiently using countercurrent 'KARR' liquid—liquid extraction column fitted with a reciprocating agitator.

11. A process as claimed in claim 1 wherein in step (xiii), the non-toxic stabilizing agent used is selected from the group consisting of mannitol, maltodextrin, β-cyclodextrin or polyvinyl alcohol.

12. A process as claimed in claim 1, wherein the final yield of bacosides within the powder with respect to dry weight of *Bacopa monniera* ranges between 1.5 to 2.5%.

13. A process as claimed in claim 1, wherein the powder obtained contains 20–30% bacosides A and B.

14. A process as claimed in claim 13, wherein the percentage of bacosides in the powder is estimated by HPTLC analysis.

* * * * *

UNITED STATES PATENT AND TRADEMARK OFFICE
CERTIFICATE OF CORRECTION

PATENT NO. : 6,833,143 B1
DATED : December 21, 2004
INVENTOR(S) : Atul Prakash Kahol et al.

It is certified that error appears in the above-identified patent and that said Letters Patent is hereby corrected as shown below:

Column 10,
Line 36, "backsides" should be -- bacosides --;

Signed and Sealed this

Third Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,833,143 B1
DATED : December 21, 2004
INVENTOR(S) : Atul Prakash Kahol et al.

It is certified that error appears in the above-identified patent and that said Letters Patent is hereby corrected as shown below:

Column 10,
Line 36, "backsides" should be -- bacosides --;

Signed and Sealed this

Fourteenth Day of June, 2005

JON W. DUDAS
*Director of the United States Patent and Trademark Office*